United States Patent [19]

Sidot et al.

[11] Patent Number: 5,332,829
[45] Date of Patent: Jul. 26, 1994

[54] PROCESS FOR REDUCING 5-(2-THENYLIDENE) HYDANTOIN TO 5-(2-THENYL) HYDANTOIN

[75] Inventors: Christian Sidot, Ezanville; Yani Christidis, Paris, both of France

[73] Assignee: Societe Francaise Hoechst, Puteaux, France

[21] Appl. No.: 14,495

[22] Filed: Feb. 8, 1993

[30] Foreign Application Priority Data

Feb. 7, 1992 [FR] France .................. 92 01414

[51] Int. Cl.$^5$ .................. C07D 409/06; C07D 233/74
[52] U.S. Cl. .................................................. 548/315.1
[58] Field of Search ...................................... 548/315.1

[56] References Cited

U.S. PATENT DOCUMENTS

| 2,729,648 | 1/1956 | Rorig | 548/315.1 |
| 4,293,563 | 10/1981 | Jamieson et al. | 548/315.1 X |
| 4,650,876 | 3/1987 | Mirviss | 548/315.1 X |

FOREIGN PATENT DOCUMENTS 0005647 5/1979 European Pat. Off. .......... 548/315.1

OTHER PUBLICATIONS

Organic Syntheses, Collective vol. 2, 1943, New York, US; pp. 489–494, H. B. Gillespie et al.: 'dl-beta Phenylalanine (Alanine, Beta-phenyl-dl-).

Chemical Abstracts, vol. 33, No. 5, Mar. 10, 1939; Columbus, Ohio, US; G. Barger et al. "Synthesis of beta-2-thienylalanine and beta-2-thienylalanine." (abrege) & Journal of Chemical Society. 1938, pp. 2100–2104.

Fieser et al, "Reagents for Organic Synthesis", vol. 1, pp. 863–864 (1967).

*Primary Examiner*—Floyd D. Higel
*Attorney, Agent, or Firm*—Browdy and Neimark

[57] ABSTRACT

Preparation process for 5-(2-thenyl) hydantoin in which 5-(2-thenylidene) hydantoin is reacted in acetic acid with a phosphorous compound selected from the group consisting of red phosphorus and phosphonic acid, in the presence of a catalytic amount of an iodine compound selected from the group consisting of iodine and hydroiodic acid.

14 Claims, No Drawings

PROCESS FOR REDUCING 5-(2-THENYLIDENE) HYDANTOIN TO 5-(2-THENYL) HYDANTOIN

The present invention relates a process for reducing 5-(2-thenylidene) hydantoin to 5-(2-thenyl) hydantoin.

5-(2-thenyl) hydantoin, as well as its precursor 5-(2-thenylidene) hydantoin, are described in the literature and are notably used for accessing producing β 2-thienyl alanine.

It known that the condensation of thiophene-2-carbaldehyde with hydantoin gives 5-(2-thenylidene) hydantoin, which can then be reduced either into 5-(2-thenyl) hydantoin, with a yield of 75% by sodium amalgam in a petroleum ether (G. BARGER and A. EASSON, J. Chem. Soc. 1938, 2100), or directly into β 2-thienyl alanine, with a yield of 72% by using ammonium sulphide (V. du VIGNEAUD et al, J. Biol. Chem., 159, 385–94, 1945).

Sodium amalgam as well as ammonium sulphide are difficult reagents to use industrially. In order to overcome this inconvenience, the Applicant has discovered with astonishment a new process allowing the conversion, with good yields, of 5-(2-thenylidene) hydantoin into 5-(2-thenyl) hydantoin.

The process according to the present invention is characterized in that the 5-(2-thenylidene) hydantoin is reacted in acetic acid with a phosphorous compound selected from the group consisting of red phosphorus and phosphonic acid, in the presence of catalytic quantities of an iodized compound selected from the group consisting of iodine and hydroiodic acid.

In the advantageous conditions for implementing the invention, the process described above is carried out in the following manner:
- at atmospheric pressure,
- under reflux of the reaction medium,
- with a molar ratio of phosphorous compound to starting product of between 1 and 5; advantageously the molar ratio of red phosphorus to starting product is about 5, and the molar ratio of phosphonic acid to starting product is about 2,
- with a molar ratio of iodine compound to starting product of between 0.01 and 0.5, the iodized derivative advantageously being hydroiodic acid in aqueous solution;
- with a molar ration of acetic acid to starting product of greater than 1.

According to a variant of the process of the invention, the process described above is carried out in the presence of water with a molar ratio of water to starting product of between 1 and 5.

The process according to the invention is carried out very easily by simple mixing of the various reagents in acetic acid. When the reaction is finished, the reaction medium cooled down to ambient temperature is poured over ice to precipitate the sought pure 5-(2-thenyl) hydantoin in the crystallized state, after possible elimination of the unconverted phosphorus in the case where it is used.

The reaction can be easily monitored by analysis by high pressure liquid chromatography of a sample taken regularly from the reaction medium.

The 5-(2-thenyl) hydantoin is easily degraded into β 2-thienyl alanine by alkaline hydrolysis (G. BARGER et al. already cited).

The following examples illustrate the present invention.

EXAMPLE 1

The following are introduced, under agitation and at ambient temperature, into a 500 ml flask containing 100 g of pure acetic acid:
- 19.4 g (0.1 mole) of pure 5-(2-thenylidene) hydantoin,
- 15.5 g (0.5 mole) of red phosphorus,
- 1.12 g of a 57% aqueous solution of hydroiodic acid, i.e. 5 mmoles,
- 1.8 g (0.1 mole) of water.

The reaction medium is heated at boiling point for 210 minutes, then after cooling down to 30° C. it is filtered to separate out the unconverted phosphorus. The filtrate is then poured over 250 g of crushed ice. The sought product crystallizes spontaneously; it is filtered and then washed two times each with 30 g of water, and finally, it is dried in an oven under reduced pressure at 60° C. to constant weight. In this way 15.6 g (0.0795 mole) of 5-(2-thenyl) hydantoin is obtained in the form of clear yellow crystals having a melting point of 189°±1° C. (reference literature M.p.=188°–190° C. G. BARGER and A. EASSON, J. Chem. Soc., 1938, 2100–4).

EXAMPLE 2

The following reaction medium is heated to boiling point:
- 19.4 g (0.1 mole) of 5-(2-thenylidene) hydantoin,
- 60 g of pure acetic acid,
- 3.6 g (0.2 mole) of water,
- 1.12 g of an aqueous solution of hydroiodic acid at 57% by weight, i.e. 5 mmoles.

A solution of 16.5 g (0.2 mole) of phosphorous acid (also called phosphorous acid) in 20.5 g of acetic acid is introduced slowly over 5 hours into the reaction medium which is maintained at boiling point. After the introduction is finished the reaction medium is maintained at boiling point for 15 hours, then it is cooled down to 30° C. and poured over 80 g of crushed ice. The sought product crystallizes spontaneously, it is filtered and washed two times each with 10 g of water, then it is dried in an oven at 60° C. under reduced pressure to constant weight. In this way 15.9 g (0.076 mole) of 5-(2-thenyl) hydantoin is obtained in the form of clear yellow crystals having a melting point of 189°±1° C.

EXAMPLE 3

A mixture constituted by:
- 1540 g of water,
- 720 g (6.43 moles) of pure 2-thiophenecarbaldehyde,
- 649 g (6.43 moles) of pure hydantoin,
- 36.6 g (0.6 mole) of monoethanolamine, is heated for 8 hours at boiling point.

After boiling for 30 minutes, the reaction solution becomes turbid and the sought 5-(2-thenylidene) hydantoin slowly precipitates.

The reaction medium is then cooled down to 15° C., then it is acidified to pH=6 with 34.8 g of 37% concentrated hydrochloric acid. The precipitate is filtered off, then washed six times with 250 g of water and finally it is dried under reduced pressure at 60° C. to constant weight. In this way 1203 g (6,195 mole) of 5-(2-thenylidene) hydantoin is obtained having a melting point greater than 260° C. (reference literature G. BARGER and A. EASSON, J. Chem. Soc., 1938, 2100-4, M.p.=253°–255° C.).

We claim:

1. A process for preparing 5-(2-thenyl) hydantoin comprising reacting 5-(2-thenylidene) hydantoin in acetic acid with a phosphorous compound selected from the group consisting of red phosphorus and phosphonic acid, in the presence of catalytic quantities of an iodine compound selected from the group consisting of iodine and hydroiodic acid.

2. Process according to claim 1, wherein said process is carried out in the presence of 1 to 5 moles of water per mole of 5-(2-thenylidene) hydantoin used.

3. Process according to claim 1 wherein the iodine compound is hydroiodic acid in aqueous solution.

4. Process according to claim 3, wherein the molar ratio of hydroiodic acid to 5-(2-thenylidene) hydantoin is between 0.01 and 0.5.

5. Process according to claim 2, wherein the iodine compound is hydroiodic acid in aqueous solution.

6. Process according to claim 5, wherein the molar ratio of hydroiodic acid to 5-(2-thenylidene) hydantoin is between 0.01 and 0.5.

7. A process for preparing 5-(2-thenyl) hydantoin comprising reacting 5-(2-thenylidene) hydantoin in acetic acid with a phosphorous compound selected from the group consisting of red phosphorous and phosphonic acid, in the presence of catalytic quantities of an iodine compound selected from the group consisting of iodine and hydroiodic acid, wherein the molar ratio of phosphorous compound to 5-(2-thenyl) hydantoin is between about 1 and 5 and the molar ratio of iodine compound to 5-(2-thenylidene) hydantoin is between 0.01 and 0.5, and thereafter recovering 5-(2-thenyl) hydantoin from the reaction medium.

8. Process according to claim 7, wherein the iodine compound is hydroiodic acid in aqueous solution.

9. Process according to claim 7, wherein the phosphorous compound is phosphoric acid.

10. A process for reducing 5-(2-thenylidene) hydantoin to 5-(2-thenyl) hydantoin consisting of reacting 5-(2-thenylidene) hydantoin in acetic acid with a phosphorous compound selected from the group consisting of red phosphorous and phosphonic acid in the presence of water and a catalytic amount of an iodine compound selected from the group consisting of iodine and hydroiodic acid wherein the molar ratio of phosphorous compound to 5-(2-thenylidene) hydantoin is between 1 and 5, the molar ratio of iodine compound to 5-(2-thenylidene) hydantoin is between 0.01 and 5, and the molar ratio of water to 5-(2-thenylidene) hydantoin is between 1 and 5, and thereafter recovering 5-(2-thenyl) hydantoin from the reaction medium.

11. Process according to claim 10, wherein the iodine compound is hydroiodic acid in aqueous solution.

12. Process according to claim 10, wherein the iodine compound is iodine.

13. Process according to claim 10, wherein the phosphorous compound is red phosphorous.

14. Process according to claim 10, wherein the phosphorous compound is phosphonic acid.

* * * * *